United States Patent [19]

Jinotti

[11] Patent Number: 4,475,379
[45] Date of Patent: Oct. 9, 1984

[54] POLLEN COUNTER

[76] Inventor: Walter Jinotti, 10 Scott St., New Brunswick, N.J. 08902

[21] Appl. No.: 421,034

[22] Filed: Sep. 22, 1982

[51] Int. Cl.³ .................. G01N 1/24; G01N 15/00
[52] U.S. Cl. ................................................ 73/28
[58] Field of Search ............. 73/28, 863.21, 863.22, 73/864.71

[56] References Cited

U.S. PATENT DOCUMENTS 2,879,664  3/1959  Tait ............................ 73/863.22
4,350,507  9/1982  Greenough ..................... 73/28

FOREIGN PATENT DOCUMENTS 2401008  8/1974  Fed. Rep. of Germany ........ 73/28
0693163  10/1979  U.S.S.R. ........................ 73/28

Primary Examiner—Stephen A. Kreitman
Assistant Examiner—Vincent P. Kovalick
Attorney, Agent, or Firm—Robert A. Green

[57] ABSTRACT

A pollen counter comprising an open-ended tube forming a path through which air can flow from one end to the other and having a fan inside the tubular member for causing air to flow at a desired rate through the tube and past a glass slide mounted within the tube and positioned to have pollen grains deposited on an edge as air flows through the tube.

5 Claims, 2 Drawing Figures

POLLEN COUNTER

BACKGROUND OF THE INVENTION

Apparatus is known for counting pollen grains in the air; however, such known apparatus does not provide a truly accurate count for various reasons. For one thing, such known apparatus measures samples over relatively long periods, say 12 to 24 hours, so that extraneous factors, such as wind, affect pollen collection. In addition, known apparatus cannot control air flow and is always subject to variations due to wind speed. Known apparatus also cannot control the volume of air flow, and, without control, accurate, useful collection cannot be made. The apparatus of the invention provides improved and more accurate collection of pollen, and it can be operated to provide meaningful collection data.

DESCRIPTION OF THE INVENTION

Figure 1:
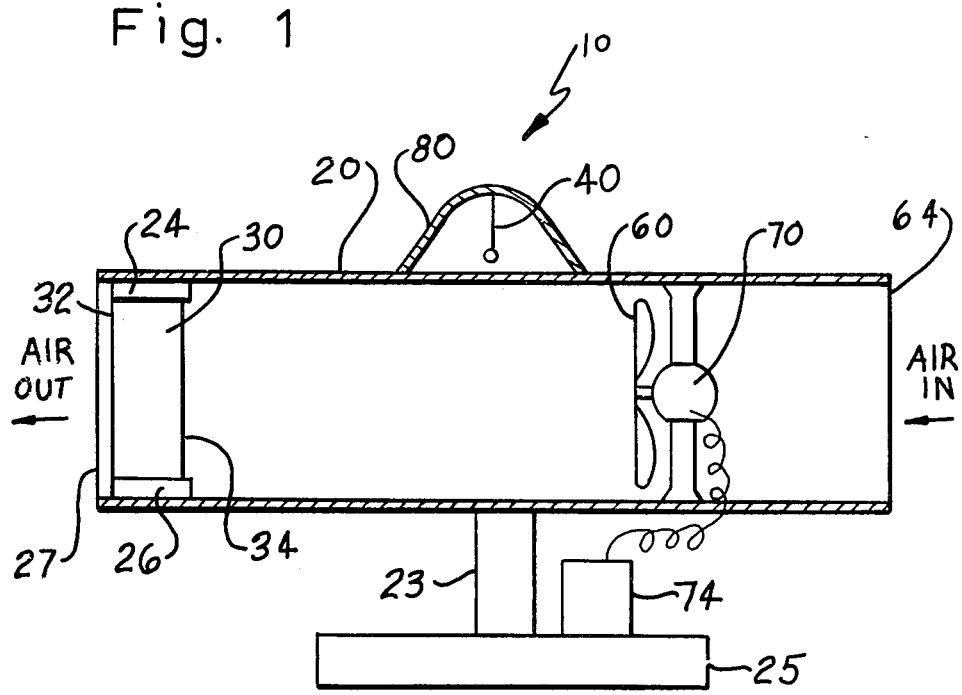
FIG. 1 is a side sectional elevational view of apparatus embodying the invention.
Figure 2:
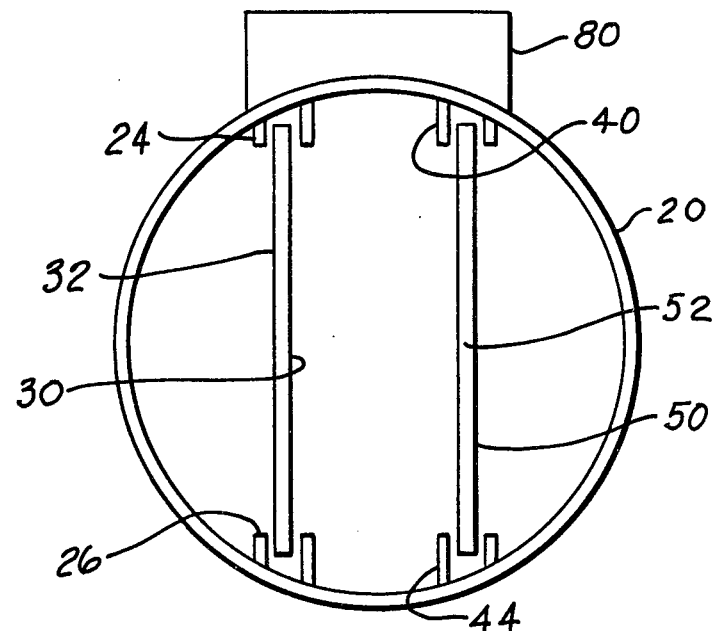
FIG. 2 is a view of the front end of the apparatus of FIG. 1.

A pollen counter 10 embodying the invention comprises a hollow, open-ended tube 20 of metal or plastic disposed horizontally and pivotably mounted on a support post 23 which itself is secured to a base 25. The tube 20 has at its front end 27 a first pair of upper and lower channels 24, 26 vertically aligned and secured to the inner wall of the tube 20 in which a glass laboratory slide 30 can be inserted so that its edges 32 and 34 face the front and rear of the tube. A second pair of upper and lower channels 40 and 44 are vertically aligned and secured to the inner walls of the tube 20 to support a second slide 50 parallel to the first and spaced about one inch therefrom, with its edges 52 and 54 facing the front and rear of the tube.

A fan 60 is mounted within the tube and oriented to draw air in the open rear end 64 of the tube, across the slides 30, 50 and out the open front end 27. The fan 60 is connected to a motor 70 whereby the speed of the fan can be adjusted to provide accurately controlled volumes of air flow through the tube. A timer 74 is also connected in the fan circuit so that its time of operation can be controlled. Timer 74 may also include the speed control means.

Mounted on the outer surface of the tube and positioned at the top of the tube is an open chamber 80 in which a weighted cord or string 90 is hung and hangs downwardly.

In using the counter 10, the timer 74 is set so that the fan 60 operates for a suitable length of time, such as continually for ten minutes, twenty minutes, or intermittently for one hour, two hours, etc. The speed is also set so that a desired volume of air flows through the tube 20 in a unit of time. A tacky substance is placed on the rear edges 34 and 54 of the slide plates 30 and 50 facing the fan 60 to catch grains of pollen, and the string 90 is observed to check wind direction. The tube 20 is rotated on its pivot support 23 to be broadside to the wind so that only air drawn by the fan passes through the tube 20. Then the fan is turned on, and, as air flows through the tube, grains of pollen, mold, etc. strike and stick to the tacky edges of the slides. After the desired time has passed, the slides are removed from the tube 20 and mounted parallel to each other in a suitable support block (not shown) with the edges which carry pollen facing up. A cover cap carrying a stain and having a diameter of about 50 mm is placed on the slides to flatten the tacky material thereon, and the collected pollen grains are counted with the aid of a microscope.

As a typical, but not limiting, example, the tub 20 is about 1½ to 2 feet long and about 3 inches to 5 inches in diameter. In addition, the two slides 30 and 50 are held about one inch apart.

In using the pollen counter, the following scale is used for reporting, with the grade reported having the indicated grains per cubic meter.

| GRADE | GRAINS/CU. METER |
| --- | --- |
| 1 | 0 |
| 2 | 1–20 |
| 3 | 20–50 |
| 4 | 50–80 |
| 5 | 80–110 |
| 6 | 110–140 |
| 7 | 140–170 |
| 8 | 170–200 |
| 9 | 230–260 |
| 10 | 260–290 |
| 11 | 290–320 |

What is claimed is:

1. A pollen counter comprising
an open-ended hollow tube forming a path through which air can flow,
a fan disposed within said tube for causing air to flow at a desired rate through said tube, and
a glass plate mounted in said tube and disposed with its edges facing the open ends of said tube whereby air which flows through said tube deposits pollen grains on an edge of said glass plate carrying tacky material which faces the air flow, said fan forcing outside air through said tube and past said glass plate whereby pollen is deposited thereon.

2. The pollen counter defined in claim 1 wherein said tube is pivotably mounted on a support so that it can be positioned broadside to any ambient wind and substantially only air drawn by the fan flows through said tube.

3. The pollen counter defined in claim 1 and including means on said tube for indicating wind direction so that said tube can be rotated and positioned broadside to the wind.

4. The apparatus defined in claim 1 wherein said fan forces pollen-containing air onto the edge of said plate which faces the fan.

5. A pollen counter comprising
an open-ended hollow tube forming a path through which air can flow and having first and second ends,
said tube being pivotably mounted on a support so that it can be positioned broadside to ambient wind,
a pollen-collecting means carrying a tacky pollen-collecting substance mounted in said tube just inside said second end thereof wherein said pollen-collecting means comprises a glass slide positioned with an edge facing said first end and is disposed so that air which flows through said tube deposits pollen grains thereon,
a fan disposed within said tube near said first end thereof for forcing air to flow at a desired rate through said tube and past said pollen-collecting means whereby pollen in the air can be deposited thereon, is forced against said edge by said fan and
control means for controlling the time and speed of operation of said fan whereby a measured quantity of pollen can be collected.

* * * * *